US010758025B2

(12) United States Patent
Le Bourhis et al.

(10) Patent No.: US 10,758,025 B2
(45) Date of Patent: Sep. 1, 2020

(54) AEROSOL DEVICE HAVING TWO COMPARTMENTS INCLUDING AN ALCOHOLIC OR HYDROALCOHOLIC HAIRSTYLING COMPOSITION, AND HAIRSTYLING METHOD

(75) Inventors: Francois Le Bourhis, Aubervilliers (FR); Jonathan Gawtrey, Boulogne (FR)

(73) Assignee: L'OREAL, Paris (FR)

( * ) Notice: Subject to any disclaimer, the term of this patent is extended or adjusted under 35 U.S.C. 154(b) by 248 days.

(21) Appl. No.: 13/993,408

(22) PCT Filed: Dec. 14, 2011

(86) PCT No.: PCT/FR2011/052988
§ 371 (c)(1),
(2), (4) Date: Dec. 2, 2013

(87) PCT Pub. No.: WO2012/080661
PCT Pub. Date: Jun. 21, 2012

(65) Prior Publication Data
US 2014/0079645 A1    Mar. 20, 2014

Related U.S. Application Data

(60) Provisional application No. 61/432,796, filed on Jan. 14, 2011, provisional application No. 61/434,064, filed on Jan. 19, 2011.

(30) Foreign Application Priority Data

Dec. 14, 2010  (FR) ..................................... 10 60475
Dec. 14, 2010  (FR) ..................................... 10 60476
Dec. 14, 2010  (FR) ..................................... 10 60477

(51) Int. Cl.
| | | |
|---|---|---|
| *A45D 34/04* | (2006.01) | |
| *A61K 8/04* | (2006.01) | |
| *A61K 8/73* | (2006.01) | |
| *A61K 8/85* | (2006.01) | |
| *A61K 8/81* | (2006.01) | |
| *A61K 8/34* | (2006.01) | |
| *A61Q 5/06* | (2006.01) | |
| *B65D 83/66* | (2006.01) | |

(52) U.S. Cl.
CPC .............. *A45D 34/04* (2013.01); *A61K 8/046* (2013.01); *A61K 8/34* (2013.01); *A61K 8/731* (2013.01); *A61K 8/8147* (2013.01); *A61K 8/8152* (2013.01); *A61K 8/85* (2013.01); *A61Q 5/06* (2013.01); *B65D 83/66* (2013.01); *A45D 2200/057* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,579,629 A | 5/1971 | Pasero et al. | |
| 3,715,428 A * | 2/1973 | Quasius et al. ................. | 424/47 |
| 3,716,633 A | 2/1973 | Viout et al. | |
| 3,734,874 A | 5/1973 | Kibler et al. | |
| 3,779,993 A | 12/1973 | Kibler et al. | |
| 3,810,977 A | 5/1974 | Levine et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,119,680 A | 10/1978 | Vachon | |
| 4,128,631 A | 12/1978 | Lundmark et al. | |
| 4,129,711 A | 12/1978 | Viout et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,300,580 A | 11/1981 | O'Neill et al. | |
| 4,973,656 A | 11/1990 | Blount | |
| 5,538,717 A | 7/1996 | La Poterie | |
| 5,595,727 A * | 1/1997 | Sturla ..................... | A61K 8/046 |
| | | | 424/47 |

(Continued)

FOREIGN PATENT DOCUMENTS

| | | |
|---|---|---|
| DE | 2 330 956 | 1/1974 |
| EP | 0 080 976 | 6/1983 |

(Continued)

OTHER PUBLICATIONS

PCT/IB/308 Form for PCT/FR2011/052988.
English language abstract of EP0080976.
English language abstract of FR2357241.

*Primary Examiner* — David J Blanchard
*Assistant Examiner* — Sarah J Chickos
(74) *Attorney, Agent, or Firm* — The Marbury Law Group, PLLC

(57) ABSTRACT

The present invention relates to a two-compartment aerosol device, comprising a styling composition in a first compartment and a compressed gas chosen from air, nitrogen and carbon dioxide, and mixtures thereof, in a second compartment. Said styling composition comprises at least one compound (A) chosen from an anionic carboxylic polymer free of urethane units, a linear sulfonic polyester and a cellulose-based compound in an alcoholic or aqueous-alcoholic medium which comprises at least 5% by weight, relative to the weight of said composition, of a $C_1$-$C_4$ monohydric alcohol. This aerosol device may constitute a hair lacquer. The invention also relates to a styling process using the device of the invention.

10 Claims, No Drawings

(56) References Cited

U.S. PATENT DOCUMENTS

| | | | |
|---|---|---|---|
| 5,660,816 A | 8/1997 | Adams et al. | |
| 5,662,893 A | 9/1997 | George et al. | |
| 5,674,479 A | 10/1997 | George et al. | |
| 6,106,813 A | 8/2000 | Mondet et al. | |
| 6,166,093 A | 12/2000 | Mougin et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 7,063,834 B2 | 6/2006 | Mougin et al. | |
| 2002/0150546 A1 | 10/2002 | Mougin et al. | |
| 2003/0191271 A1 | 10/2003 | Mondet et al. | |
| 2004/0042974 A1* | 3/2004 | Dupuis et al. | 424/47 |
| 2004/0047812 A1* | 3/2004 | Pataut | A61K 8/046 424/47 |
| 2006/0024259 A1* | 2/2006 | Vrignaud | A61K 8/737 424/70.11 |

FOREIGN PATENT DOCUMENTS

| | | |
|---|---|---|
| EP | 0 648 485 | 10/1993 |
| EP | 0 619 111 | 10/1994 |
| EP | 0 637 600 | 2/1995 |
| EP | 0 751 162 | 1/1997 |
| EP | 0656021 | 10/1997 |
| EP | 1629829 A * | 3/2006 |
| FR | 1222944 | 6/1960 |
| FR | 1400366 | 4/1965 |
| FR | 1564110 | 3/1969 |
| FR | 1580545 | 9/1969 |
| FR | 2077143 | 10/1971 |
| FR | 2198719 | 4/1974 |
| FR | 2265781 | 10/1975 |
| FR | 2265782 | 10/1975 |
| FR | 2350384 | 12/1977 |
| FR | 2357241 | 2/1978 |
| FR | 2393573 | 1/1979 |
| FR | 2439798 | 5/1980 |
| FR | 2743297 | 7/1997 |
| GB | 839 805 | 6/1960 |
| GB | 922 457 | 4/1963 |
| GB | 1 021 400 | 3/1966 |
| GB | 1 408 388 | 10/1975 |
| GB | 1 572 626 | 7/1980 |
| LU | 75370 | 2/1978 |
| LU | 75371 | 2/1978 |
| WO | 94/03510 | 2/1994 |

* cited by examiner

AEROSOL DEVICE HAVING TWO COMPARTMENTS INCLUDING AN ALCOHOLIC OR HYDROALCOHOLIC HAIRSTYLING COMPOSITION, AND HAIRSTYLING METHOD

This is a national stage application of PCT/FR2011/052988, filed internationally on Dec. 14, 2011, which claims priority to U.S. Provisional Application Nos. 61/432,796, filed on Jan. 14, 2011 and 61/434,064, filed Jan. 19, 2011; as well as French Application Nos. 1060475, filed on Dec. 14, 2010, 1060476, filed on Dec. 14, 2010 and 1060477, filed on Dec. 14, 2010, all of which are incorporated herein by reference in their entireties.

The present invention relates to a two-compartment aerosol device comprising a styling composition and a particular compressed gas, and to a styling process.

Styling compositions, such as lacquers and sprays, conditioned in aerosol spray form, are generally composed of a liquid phase comprising, in a cosmetically acceptable aqueous, alcoholic or aqueous-alcoholic medium, at least one fixing polymer, and a propellant, which is a liquefied gas under reduced pressure or dissolved in the liquid phase.

Other aerosol devices comprising such a liquid phase exist, but they comprise compressed gases for propelling the liquid phase. However, these compressed-gas devices have the drawback of losing gas pressure over time. Specifically, leakage of the compressed gases is observed over time or in the event of incorrect use of the container, i.e. when it is turned upside down.

This drawback results in poorer propulsion of the liquid phase over time and, consequently, poorer distribution of the liquid phase on the hair.

Another factor that may lead to poor distribution of the liquid phase from these devices is the quality of the spray, which degrades when it is sought to obtain the greatest possible fixing, i.e. when it is sought to increase the amount of polymer that can be dissolved in said liquid phase.

The Applicant has discovered, surprisingly, that the mechanical separation of the liquid phase from the compressed gas producing the propulsion, and the use of a particular compressed gas and of a compound chosen from an anionic carboxylic polymer free of urethane units, a linear sulfonic polyester and a cellulose-based compound in the propelled composition makes it possible to solve the problems of leakage and of distribution of the liquid phase on the hair. This particular combination thus makes it possible to obtain fixing and/or shaping with a level of fixing that cannot usually be achieved with this type of product.

A subject of the invention is therefore a two-compartment aerosol device comprising a styling composition which comprises at least one compound (A) chosen from:
an anionic carboxylic polymer free of urethane units;
a linear sulfonic polyester;
a cellulose-based compound;
and at least one compressed gas as described below.

Another subject of the present invention consists of a styling process using this device.

Other subjects, characteristics, aspects and advantages of the invention will emerge even more clearly on reading the description and the various examples that follow.

The two-compartment aerosol device according to the invention comprises:
(a) in a first compartment, a styling composition comprising at least one compound (A) chosen from:
an anionic carboxylic polymer free of urethane units;
a linear sulfonic polyester;
a cellulose-based compound;
in an alcoholic or aqueous-alcoholic medium which comprises at least 5% by weight, relative to the total weight of said composition, of a $C_1$-$C_4$ monohydric alcohol, and
(b) in a second compartment, a compressed gas chosen from air, nitrogen and carbon dioxide, and mixtures thereof, air being particularly preferred.

Said compressed gas is preferably used at a pressure of between 1 and 12 bar and even better still between 9 and 11 bar.

In the text hereinabove or hereinbelow, the expression "at least one" is equivalent to "one or more".

Non-Polyurethane Anionic Carboxylic Fixing Polymer (Free of Urethane Units)

The anionic fixing polymers which can be used according to the invention are polymers comprising groups derived from carboxylic acid and which preferably have a number-average molecular weight of between approximately 500 and 5 000 000.

The carboxylic groups are provided by unsaturated monocarboxylic or dicarboxylic acid monomers such as those corresponding to the formula:

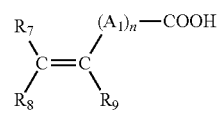

(I)

in which n is an integer from 0 to 10, A1 denotes a methylene group optionally joined to the carbon atom of the unsaturated group or to the adjacent methylene group when n is greater than 1, via a heteroatom such as oxygen or sulfur, R7 denotes a hydrogen atom or a phenyl or benzyl group, R8 denotes a hydrogen atom or a lower alkyl or carboxyl group, and R9 denotes a hydrogen atom, a lower alkyl group, a group —$CH_2$—COOH or a phenyl or benzyl group.

In the abovementioned formula, a lower alkyl group preferably denotes a group having 1 to 4 carbon atoms, and in particular the methyl and ethyl groups.

The anionic fixing polymers containing carboxylic groups may be:

A) copolymers of acrylic acid and of acrylamide such as those sold in the form of their sodium salts under the names Reten 421, 423 or 425 by the company Hercules, the sodium salts of polyhydroxycarboxylic acids;

B) copolymers of acrylic or methacrylic acid with a monoethylenic monomer such as ethylene, styrene, vinyl esters and acrylic or methacrylic acid esters, optionally grafted onto a polyalkylene glycol such as polyethylene glycol and optionally crosslinked. Such polymers are described in particular in patent applications FR 1 222 944 and DE 2 330 956, the copolymers of this type comprising an optionally N-alkylated and/or hydroxyalkylated acrylamide unit in their chain as described in particular in patent applications LU 75370 and LU 75371 or sold under the name Quadramer by the company American Cyanamid. Mention may also be made of methacrylic acid/ethyl acrylate/tert-butyl acrylate terpolymers such as the product sold under the name Luvimer® 100 P by the company BASF.

Mention may also be made of methacrylic acid/acrylic acid/ethyl acrylate/methyl methacrylate copolymers as an aqueous dispersion, sold under the name Amerhold® DR 25 by the company Amerchol.

Mention may also be made of polymers of the type Fixate G 100;

C) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Such polymers are described, inter alia, in patent applications FR 1 222 944, FR 1 580 545, FR 2 265 782, FR 2 265 781, FR 1 564 110 and FR 2 439 798. Commercial products that come under this category are the resins 28-29-30, 26-13-14 and 28-13-10 sold by the company National Starch;

D) copolymers of $C_4$-$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and esters thereof, the anhydride functions of these copolymers optionally being monoesterified or monoamidated. Such polymers are described in particular in patent applications U.S. Pat. No. 2,047,398, U.S. Pat. No. 2 723 248, U.S. Pat. No. 2,102,113 and GB 839 805. Commercial products are in particular those sold under the names Gantrez® AN or ES by the company ISP;

copolymers comprising (i) one or more maleic, citraconic or itaconic anhydride units and (ii) one or more monomers chosen from allyl or methallyl esters optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in patent applications FR 2 350 384 and FR 2 357 241 by the Applicant;

E) polyacrylamides comprising carboxylate groups.

The anionic carboxylic fixing polymers are preferably chosen from acrylic acid copolymers, such as the acrylic acid/ethyl acrylate/N-tert-butylacrylamide terpolymers sold especially under the name Ultrahold® Strong by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold especially under the name Resin 28-29-30 by National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by ISP, the copolymers of methacrylic acid and of methyl methacrylate sold under the name Eudragit® L by Rohm Pharma, the copolymers of methacrylic acid and of ethyl acrylate sold under the name Luvimer® MAEX or MAE by BASF, the vinyl acetate/crotonic acid copolymers sold especially under the name Luviset CA 66 by BASF, and the vinyl acetate/crotonic acid copolymers grafted with polyethylene glycol sold under the name Aristoflex® A by BASF.

The fixing polymers of the invention may also be polymers with a silicone backbone bearing non-silicone grafts or non-silicone polymers with silicone grafts, bearing carboxylic groups, such as the polymer VS80 from the company 3M.

Among the anionic fixing polymers mentioned above, it is more particularly preferred to use the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, and the copolymers of methacrylic acid and of ethyl acrylate sold under the name Luvimer® MAEX or MAE by the company BASF.

When they are present, the anionic carboxylic fixing polymer(s) are preferably present in an amount ranging from 0.5% to 20% by weight and even better still from 1% to 12% by weight relative to the total weight of the styling composition.

Linear Sulfonic Polyester

The composition according to the invention may comprise at least one linear sulfonic polyester.

The term "sulfonic polyester" is intended to mean a polyester comprising one or more sulfonic groups, which are in free form or partially or even totally salified.

This linear sulfonic polyester is water-soluble or water-dispersible.

The term "water-dispersible linear sulfonic polyester" is intended to mean any sulfonic polyester which has an ability to form a dispersion, i.e. a two-phase system in which the first phase is made up of finely divided particles uniformly distributed in the second phase which is the continuous phase.

The term "sulfonic polyester" is preferably intended to mean copolyesters obtained by polycondensation of at least one dicarboxylic acid or of an ester thereof, or of at least one diol and of at least one sulfoaryldicarboxylic difunctional compound substituted on the aromatic nucleus with a —$SO_3M$ group in which M represents a hydrogen atom or a metal ion such as $Na^+$, $Li^+$ or $K^+$.

The linear sulfonic polyesters of the invention generally have a weight-average molecular weight between approximately 1000 and 60 000, and preferably from 4000 to 20 000, as determined by gel permeation chromatography (or GPC).

The glass transition temperature (Tg) of these sulfonic polyesters is generally included in the range of from 10° C. to 100° C. Preferably, the Tg of the polyester(s) used is greater than or equal to 50° C.

The glass transition temperature (Tg) is measured by differential scanning calorimetry (DSC) according to standard ASTM D3418-97.

Preferably, the linear polyesters of the invention are water-dispersible.

The linear sulfonic polyesters of the invention are described in greater detail in patent applications U.S. Pat. No. 3,734,874, U.S. Pat. No. 3,779,993, U.S. Pat. No.

4,119,680, U.S. Pat. No. 4,300,580, U.S. Pat. No. 4,973,656, U.S. Pat. No. 5,660,816, U.S. Pat. No. 5,662,893 and U.S. Pat. No. 5,674,479.

The sulfonic polyesters preferably used in the invention comprise at least units derived from isophthalic acid, from a sulfoaryldicarboxylic acid salt and from diethylene glycol and more particularly the sulfonic polyesters used in the invention are obtained from isophthalic acid, from sulfoisophthalic acid sodium salt, from diethylene glycol and from 1,4-cyclohexanemethanol.

By way of examples of a sulfonic polyester, mention may in particular be made of those known under the INCI name Diglycol/CHDM/Isophthalates/SIP and sold under the trade names Eastman AQ Polymer (AQ35S, AQ38S, AQ55S and AQ48 Ultra) by the company Eastman Chemical.

Preferably, the Tg of the polyester(s) used is greater than or equal to 50° C.

When they are present, the linear sulfonic polyester(s) are preferably present in an amount ranging from 0.5% to 20% by weight and even better still from 1% to 12% by weight relative to the total weight of the styling composition.

Cellulose-Based Compound

The composition according to the invention may comprise at least one cellulose-based compound.

The term "cellulose-based compound" is intended to mean, according to the invention, any polysaccharide compound having in its structure sequences of glucose residues bonded together via β-1,4 linkages.

The cellulose-based compounds can be celluloses per se, including in a microcrystalline form, and cellulose ethers. The cellulose ethers are preferably chosen from non-ionic, anionic or cationic ethers.

Among the non-ionic cellulose ethers, mention may be made of alkylcelluloses such as methylcelluloses and ethylcelluloses or hydroxyalkylcelluloses such as hydroxymethylcelluloses, hydroxyethylcelluloses and hydroxypropylcelluloses, and mixed hydroxyalkylalkylcelluloses such as hydroxypropylmethylcelluloses, hydroxyethylmethylcelluloses, hydroxyethylethylcelluloses and hydroxybutylmethylcelluloses.

Among the anionic compounds, mention may be made of carboxyalkylcelluloses and salts thereof. By way of example, mention may be made of carboxymethylcelluloses, carboxymethylmethyl-celluloses and carboxymethylhydroxyethylcelluloses and sodium salts thereof.

Among the cationic compounds, mention may be made of crosslinked or non-crosslinked, quaternized hydroxyethylcelluloses. The quaternizing agent may in particular be glycidyltrimethylammonium chloride or a fatty amine such as laurylamine or stearylamine. Another cationic cellulose that may be mentioned is hydroxyethylcellulosehydroxypropyltrimethylammonium.

Preferably, the cellulose-based compound of the invention is non-ionic.

Even more preferentially, the cellulose-based compound is a hydroxypropylcellulose.

When they are present, the cellulose-based compound(s) are preferably present in an amount ranging from 0.5% to 20% by weight and even better still from 1% to 12% by weight relative to the total weight of the styling composition.

Cosmetic Medium

The compositions of the invention comprise at least one $C_1$-$C_4$ monohydric alcohol.

The term "monohydric" is intended to mean an alcohol comprising only one hydroxyl function.

The monohydric alcohols of the invention are preferably chosen from ethanol, isopropanol, n-propanol and tert-butanol, or mixtures thereof.

Preferably, they are chosen from ethanol and isopropanol, or mixtures thereof.

Even more preferentially, the $C_1$-$C_4$ monohydric alcohol is ethanol.

The medium comprises at least 5% by weight, preferably from 5% to 99.9% by weight, even better still from 10% to 99% by weight and even more preferentially from 20% to 98% by weight, relative to the total weight of said composition, of one or more $C_1$-$C_4$ monohydric alcohols.

In an aqueous-alcoholic medium, the proportion of water may range from 1% to 95% and preferably from 10% to 90% of the total weight of the composition.

According to one particular embodiment, the composition according to the invention may also comprise one or more additional fixing polymers.

For the purposes of the present invention, the term "fixing polymer" is intended to mean any polymer that can impart a given shape or hold a given shape or hairstyle.

The additional synthetic fixing polymers are generally chosen from cationic, amphoteric, non-ionic and anionic polymers and mixtures thereof, other than the compound(s) (A) already contained in the composition.

For the purposes of the present invention, the term "cationic polymer" is intended to mean any polymer comprising cationic groups and/or groups that can be ionized into cationic groups.

The cationic fixing polymers may be chosen from polymers comprising primary, secondary, tertiary and/or quaternary amine groups forming part of the polymer chain or directly attached thereto, and having a number-average molecular weight of between 500 and approximately 5 000 000 and preferably between 1000 and 3 000 000.

Among these polymers, mention may be made more particularly of the following cationic polymers:

(1) homopolymers or copolymers of acrylic or methacrylic esters or amides with amine functions, and comprising at least one of the units of the following formulae:

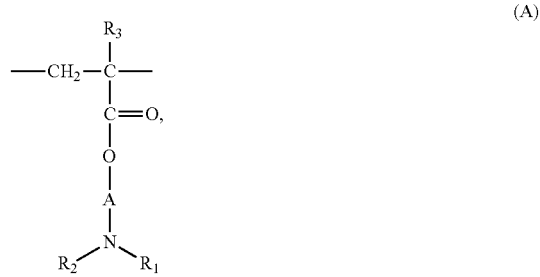

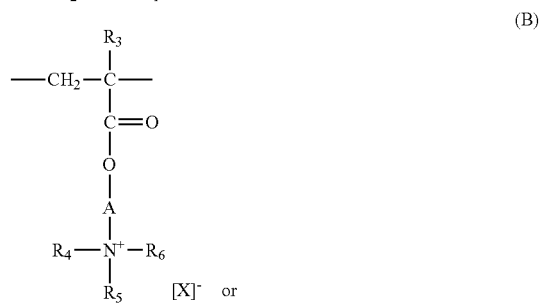

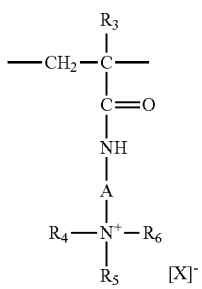
(C)

in which:

R1 and R2, which may be identical or different, each represent a hydrogen atom or an alkyl group containing from 1 to 6 carbon atoms; R3 denotes a hydrogen atom or a $CH_3$ group; A is a linear or branched alkyl group comprising from 1 to 6 carbon atoms or a hydroxyalkyl group comprising from 1 to 4 carbon atoms; R4, R5 and R6, which may be identical or different, represent an alkyl group containing from 1 to 18 carbon atoms or a benzyl group; $X^-$ denotes a methosulfate anion or a halide such as chloride or bromide.

These copolymers also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyllactams such as vinylpyrrolidone or vinylcaprolactam, and vinyl esters.

Thus, among these copolymers, mention may be made of:

copolymers of acrylamide and of dimethylaminoethyl methacrylate which are quaternized with dimethyl sulfate or with a dimethyl halide, such as the product sold under the name Hercofloc® by the company Hercules, copolymers of acrylamide and of methacryloyloxyethyltrimethylammonium chloride which are described, for example, in patent application EP-A-080 976 and are sold under the name Bina Quat P 100 by the company Ciba Geigy, copolymers of acrylamide and of methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in patent applications FR 2 077 143 and FR 2 393 573, dimethylaminoethyl methacrylate/vinylcaprolactam/vinylpyrrolidone terpolymers such as the product sold under the name Gaffix® VC 713 by the company ISP, and quaternized vinylpyrrolidone/dimethylaminopropyl methacrylamide copolymers such as, in particular, the product sold under the name Gafquat® HS 100 by the company ISP;

(2) quaternary copolymers of vinylpyrrolidone and of vinylimidazole.

The amphoteric fixing polymers may be chosen from polymers comprising units B and C distributed randomly in the polymer chain, in which B denotes a unit derived from a monomer comprising at least one basic nitrogen atom and C denotes a unit derived from an acid monomer comprising one or more carboxylic or sulfonic groups, or alternatively B and C can denote groups derived from carboxybetaine or sulfobetaine zwitterionic monomers;

B and C may also denote a cationic polymer chain comprising primary, secondary, tertiary or quaternary amine groups, in which at least one of the amine groups bears a carboxylic or sulfonic group connected via a hydrocarbon-based group or alternatively B and C form part of a chain of a polymer containing an α,β-dicarboxylic ethylene unit in which one of the carboxylic groups has been made to react with a polyamine comprising one or more primary or secondary amine groups.

The amphoteric fixing polymers corresponding to the definition given above may be chosen from the following polymers:

(1) copolymers having acidic vinyl units and basic vinyl units, such as those resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamides and acrylamides. Such compounds are described in patent U.S. Pat. No. 3,836,537, (2) polymers comprising units deriving from:

a) at least one monomer chosen from acrylamides and methacrylamides substituted on the nitrogen atom with an alkyl group, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly used are compounds in which the alkyl groups contain from 2 to 12 carbon atoms, and more particularly N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

They are more particularly the copolymers whose CTFA (4th edition, 1991) name is octylacrylamide/acrylates/butylaminoethyl methacrylate copolymer, such as the products sold under the name Amphomer® or Lovocryl® 47 by the company National Starch;

(3) crosslinked and acylated polyaminoamides partially or totally deriving from polyaminoamides of general formula:

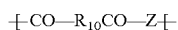 (XVII)

in which R10 represents a divalent group derived from a saturated dicarboxylic acid, a mono- or dicarboxylic aliphatic acid containing an ethylenic double bond, an ester of a lower alkanol, containing 1 to 6 carbon atoms, of these acids, or a group deriving from the addition of any one of said acids to a bis(primary) or bis(secondary) amine, and Z denotes a group deriving from a bis(primary), mono(secondary) or bis(secondary) polyalkylene-polyamine and preferably represents:

a) in proportions of from 60 to 100 mol %, the group:

 (XVIII)

where x=2 and p=2 or 3, or alternatively x=3 and p=2, this group being derived from diethylenetriamine, triethylenetetramine or dipropylenetriamine;

b) in proportions of from 0 to 40 mol %, the group (XVIII) above in which x=2 and p=1 and which is derived from ethylenediamine, or the group derived from piperazine:

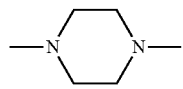

c) in proportions of from 0 to 20 mol %, the group —NH—(CH$_2$)$_6$—NH— derived from hexamethylenediamine, these polyaminoamides being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyaminoamide and acylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the acylation are preferably propane sultone or butane sultone; the salts of the acylating agents are preferably the sodium or potassium salts;

(4) polymers comprising zwitterionic units of formula:

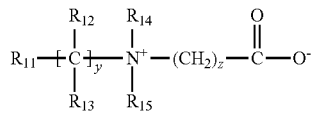

in which R11 denotes a polymerizable unsaturated group such as an acrylate, methacrylate, acrylamide or methacrylamide group, y and z represent an integer from 1 to 3, R12 and R13 represent a hydrogen atom, a methyl, ethyl or propyl group, R14 and R15 represent a hydrogen atom or an alkyl group such that the sum of the carbon atoms in R14 and R15 does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

By way of example, mention may be made of the copolymers of methyl methacrylate/methyl dimethylcarboxymethylammonioethyl methacrylate such as the product sold under the name Diaformer Z301 by the company Sandoz;

(5) polymers derived from chitosan comprising monomer units corresponding to the following formulae:

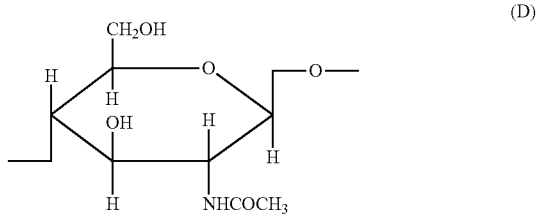

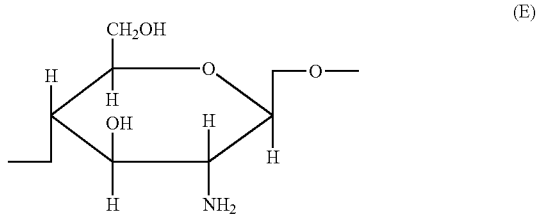

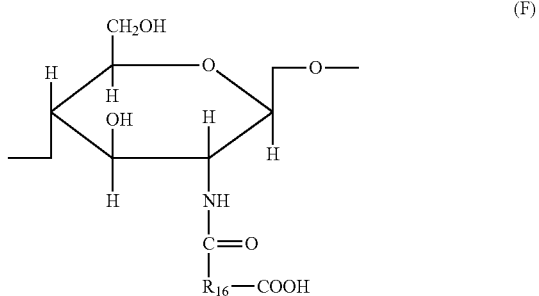

the unit (D) being present in proportions of between 0 and 30%, the unit (E) in proportions of between 5% and 50% and the unit (F) in proportions of between 30% and 90%, it being understood that, in this unit (F), R16 represents a group of formula:

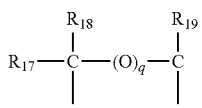

in which, if q=0, R17, R18 and R19, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, an alkylthio residue in which the alkyl group bears an amino residue, at least one of the groups R17, R18 and R19 being, in this case, a hydrogen atom;

or, if q=1, R17, R18 and R19 each represent a hydrogen atom, and also the salts formed by these compounds with bases or acids;

(6) polymers containing units corresponding to the general formula (XIX), which are described, for example, in patent FR 1 400 366:

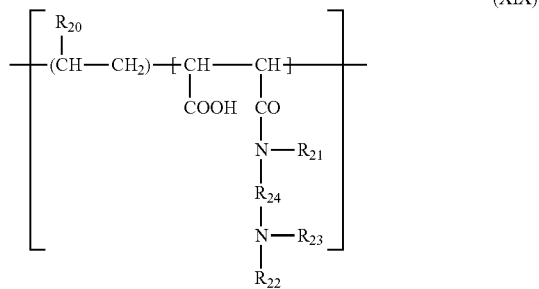

in which R20 represents a hydrogen atom, a CH$_3$O, CH$_3$CH$_2$O or phenyl group, R21 denotes a hydrogen atom or a lower alkyl group such as methyl or ethyl, R22 denotes a hydrogen atom or a C$_1$-C$_6$ lower alkyl group such as methyl or ethyl, R23 denotes a C$_1$-C$_6$ lower alkyl group such as methyl or ethyl or a group corresponding to the formula: —R24—N(R22)$_2$, R24 representing a group —CH$_2$—CH$_2$—, —CH$_2$—CH$_2$—CH$_2$— or —CH$_2$—CH(CH$_3$)—, R22 having the meanings mentioned above;

(7) polymers derived from the N-carboxyalkylation of chitosan, such as N-carboxymethyl chitosan or N-carboxybutyl chitosan, sold under the name Evalsan by the company Jan Dekker;

(8) amphoteric polymers of the -D-X-D-X type chosen from:

a) polymers obtained via the action of chloroacetic acid or sodium chloroacetate on compounds comprising at least one unit of formula:

-D-X-D-X-D-      (XX)

where D denotes a group

and X denotes the symbol E or E', E or E', which may be identical or different, denoting a divalent group that is an alkylene group with a straight or branched chain containing up to 7 carbon atoms in the main chain, which is unsubstituted or substituted by hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) the polymers of formula:

D-X-D-X-      (XXI')

where D denotes a group

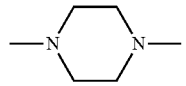

and X denotes the symbol E or E' and at least once E'; E having the meaning given above and E' being a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate;

(9) (C$_1$-C$_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers may also comprise other vinyl comonomers, such as vinylcaprolactam.

Among the amphoteric fixing polymers described above, the ones that are most particularly preferred are those of class (3), such as the copolymers whose CTFA name is Octylacrylamide/acrylates/butylaminoethyl methacrylate copolymer, such as the products sold under the names Amphomer®, Amphomer® LV 71 or Lovocryl® 47 by National Starch and those of class (4) such as the copolymers of methyl methacrylate/methyl dimethylcarboxymethylammonioethyl methacrylate, sold, for example, under the name Diaformer® Z301 by Sandoz.

The non-ionic fixing polymers that may be used according to the present invention are chosen, for example, from:
polyalkyloxazolines;
vinyl acetate homopolymers;
vinyl acetate copolymers, for instance copolymers of vinyl acetate and of acrylic ester, copolymers of vinyl acetate and of ethylene, or copolymers of vinyl acetate and of maleic ester, for example of dibutyl maleate;
acrylic ester homopolymers and copolymers, for instance copolymers of alkyl acrylates and of alkyl methacrylates, such as the products sold by Röhm & Haas under the names Primal® AC-261 K and Eudragit® NE 30 D, by BASF under the name 8845, or by Hoechst under the name Appretan® N9212;
acrylonitrile copolymers and copolymers of a non-ionic monomer chosen, for example, from butadiene and alkyl (meth)acrylates; mention may be made of the products sold under the name CJ 0601 B by the company Röhm & Haas;
styrene homopolymers;
styrene copolymers, for instance copolymers of styrene and of alkyl (meth)acrylate, such as the products Mowilith® LDM 6911, Mowilith® DM 611 and Mowilith® LDM 6070 sold by Hoechst, and the products Rhodopas® SD 215 and Rhodopas® DS 910 sold by Rhodia Chimie; copolymers of styrene, of alkyl methacrylate and of alkyl acrylate; copolymers of styrene and of butadiene; or copolymers of styrene, of butadiene and of vinylpyridine;
polyamides;
vinyllactam homopolymers such as polyvinylpyrrolidone; and
vinyllactam copolymers such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF; and poly(vinylpyrrolidone/vinyl acetate/vinyl propionate) terpolymers, for instance the product sold under the name Luviskol® VAP 343 by the company BASF.

The alkyl groups of the non-ionic polymers mentioned above preferably contain from 1 to 6 carbon atoms.

The additional anionic fixing polymers may be polymers comprising groups derived from carboxylic acid, sulfonic acid or phosphoric acid and have a number-average molecular weight of between approximately 500 and 5 000 000.

The carboxylic groups are provided by unsaturated monocarboxylic or dicarboxylic acid monomers such as those corresponding to the formula:

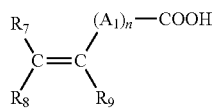

in which n is an integer from 0 to 10, A1 denotes a methylene group optionally joined to the carbon atom of the unsaturated group or to the adjacent methylene group when n is greater than 1, via a heteroatom such as oxygen or sulfur, R7 denotes a hydrogen atom or a phenyl or benzyl group, R8 denotes a hydrogen atom or a lower alkyl or carboxyl group, and R9 denotes a hydrogen atom, a lower alkyl group, a group —$CH_2$—COOH or a phenyl or benzyl group.

In the abovementioned formula, a lower alkyl group preferably denotes a group having 1 to 4 carbon atoms, and in particular the methyl and ethyl groups.

The anionic fixing polymers containing carboxylic groups may be:

A) copolymers of acrylic acid and of acrylamide sold in the form of their sodium salts under the names Reten 421, 423 or 425 by the company Hercules, the sodium salts of polyhydroxycarboxylic acids;

B) copolymers of acrylic or methacrylic acid with a monoethylenic monomer such as ethylene, styrene, vinyl esters and acrylic or methacrylic acid esters, optionally grafted onto a polyalkylene glycol such as polyethylene glycol and optionally crosslinked. Such polymers are described in particular in patent applications FR 1 222 944 and DE 2 330 956, the copolymers of this type comprising an optionally N-alkylated and/or hydroxyalkylated acrylamide unit in their chain as described in particular in patent applications LU 75370 and LU 75371 or sold under the name Quadramer by the company American Cyanamid. Mention may also be made of methacrylic acid/ethyl acrylate/tert-butyl acrylate terpolymers such as the product sold under the name Luvimer® 100 P by the company BASF.

Mention may also be made of methacrylic acid/acrylic acid/ethyl acrylate/methyl methacrylate copolymers as an aqueous dispersion, sold under the name Amerhold® DR 25 by the company Amerchol.

Mention may also be made of polymers of the type Fixate G 100;

C) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Such polymers are described, inter alia, in patent applications FR 1 222 944, FR 1 580 545, FR 2 265 782, FR 2 265 781, FR 1 564 110 and FR 2 439 798. Commercial products that come under this category are the resins 28-29-30, 26-13-14 and 28-13-10 sold by the company National Starch;

D) copolymers of $C_4$-$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and esters thereof, the anhydride functions of these copolymers optionally being monoesterified or monoamidated. Such polymers are described in particular in patent applications U.S. Pat. No. 2,047,398, U.S. Pat. No. 2,723,248, U.S. Pat. No. 2,102,113 and GB 839 805. Commercial products are in particular those sold under the names Gantrez® AN or ES by the company ISP;

copolymers comprising (i) one or more maleic, citraconic or itaconic anhydride units and (ii) one or more monomers chosen from allyl or methallyl esters optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in patent applications FR 2 350 384 and FR 2 357 241 by the Applicant;

E) polyacrylamides comprising carboxylate groups.

The homopolymers and copolymers comprising sulfonic groups are polymers comprising vinylsulfonic, styrenesulfonic, naphthalenesulfonic or acrylamidoalkylsulfonic units. They are different from the linear sulfonic polyesters of the invention.

These polymers can be chosen in particular from:

polyvinylsulfonic acid salts having a molecular weight of between approximately 1000 and 100 000, and also the copolymers with an unsaturated comonomer such as acrylic or methacrylic acids and esters thereof, and also acrylamide or derivatives thereof, vinyl ethers and vinylpyrrolidone;

polystyrenesulfonic acid salts such as the sodium salts sold, for example, under the names Flexan® 500 and Flexan® 130 by National Starch. These compounds are described in patent FR 2 198 719;

polyacrylamidesulfonic acid salts, such as those mentioned in patent U.S. Pat. No. 4,128,631 and more particularly the polyacrylamidoethylpropanesulfonic acid sold under the name Cosmedia Polymer HSP 1180 by Henkel;

branched sulfonic polyesters, such as the product sold under the name AQ 1350.

The anionic fixing polymers are preferably chosen from acrylic acid copolymers, such as the acrylic acid/ethyl acrylate/N-tert-butylacrylamide terpolymers sold especially under the name Ultrahold® Strong by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold especially under the name Resin 28-29-30 by National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by ISP, the copolymers of methacrylic acid and of methyl methacrylate sold under the name Eudragit® L by Rohm Pharma, the copolymers of methacrylic acid and of ethyl acrylate sold under the name Luvimer® MAEX or MAE by BASF, the vinyl acetate/crotonic acid copolymers sold under the name Luviset CA 66 by BASF, and the vinyl acetate/crotonic acid copolymers grafted with polyethylene glycol sold especially under the name Aristoflex® A by BASF.

The fixing polymers of the invention may also be polymers with a silicone backbone bearing non-silicone grafts or non-silicone polymers with silicone grafts, such as the polymer VS80 from the company 3M.

Among the anionic fixing polymers mentioned above, it is more particularly preferred to use the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, and the copolymers of methacrylic acid and of ethyl acrylate sold under the name Luvimer® MAEX or MAE by the company BASF.

As fixing polymers, it is also possible to use functionalized or non-functionalized, cationic, non-ionic, anionic or amphoteric, silicone or non-silicone polyurethanes, or mixtures thereof.

The polyurethanes particularly targeted by the present invention are those described in patent applications EP 0 751 162, EP 0 637 600, EP 0 648 485 and FR 2 743 297, of which the Applicant is the proprietor, and also in patent applications EP 0 656 021 and WO 94/03510 from the company BASF and EP 0 619 111 from the company National Starch.

Polyurethanes particularly suitable in the present invention may include the products sold under the names Luviset PUR® and Luviset® Si PUR by BASF.

The additional fixing polymer(s) are preferably not polyurethanes.

The additional fixing polymer(s) are preferably anionic or non-ionic.

When they are present, the additional fixing polymer(s) represent from 0.1% to 20% by weight and better still from 0.5% to 10% by weight relative to the total weight of the composition.

The styling composition may also comprise additives such as silicones in soluble, dispersed or microdispersed form, treating active agents, moisturizers such as glycerol, UV-screening agents, acids, bases, plasticizers, solubilizers, preserving agents, vitamins and provitamins, dyes, pigments, anionic, cationic, non-ionic or amphoteric surfactants, fragrances and anticorrosion agents, and mixtures thereof.

Those skilled in the art will take care to select the optional additives and the amount thereof such that they do not harm the properties of the compositions of the present invention.

These additives are especially present in the composition according to the invention in an amount ranging from 0 to 20% by weight relative to the total weight of the composition.

Preferably, the two-compartment aerosol device is formed from an external aerosol can comprising an inner pouch hermetically welded to a valve. The composition is introduced into the inner pouch and a compressed gas is introduced between the pouch and the can at a pressure sufficient to make the product come out in the form of a spray through a nozzle orifice. Such a device is sold under the name EP Spray by the company EP-Spray System SA.

The aerosol devices of the invention are preferably hair lacquers.

The present invention also relates to a styling process, which consists in that the styling composition contained in the aerosol device according to the invention is vapourized onto wet or dry hair, and, generally, the hair is dried with a heating device (hairdryer, hood, etc.) or is left to dry freely.

The following examples are given as illustrations of the present invention without being limiting in nature.

All the amounts are indicated as weight percentages of active materials relative to the total weight of the composition.

The styling compositions were prepared from the following ingredients:

EXAMPLE 1

| | |
|---|---|
| Vinyl acetate/crotonic acid copolymer (90/10) (Luviset CA 66 from BASF) | 5.00 |
| Aminomethylpropanol | qs 95-100% neutralization |
| Fragrance | 0.10 |
| Ethyl alcohol qs | 100 |

EXAMPLE 2

| | |
|---|---|
| Polyester-5 (AQ 48 Ultra Polymer from Eastman) (Expressed by weight of polymer) | 5.00 |
| Demineralized water | 40 |
| Fragrance | 0.10 |
| Ethyl alcohol qs | 100 |

EXAMPLE 3

| | Composition A | Composition B |
|---|---|---|
| Hydroxypropylcellulose (Klucel EF Pharm from Ashland) | 3 | 3 |
| Demineralized water | 18 | 18 |
| Glycerol | — | 0.3 |
| Ethyl alcohol qs | qs 100 | qs 100 |

Each of the compositions prepared above was introduced into an aerosol dispensing device sold under the name EP Spray by the company EP Spray System S.A. described above. A valve of reference 6001 format D6 is fixed onto a standard aerosol can, and the diffuser is a turbulent-nozzle diffuser.

The pouch is filled with the composition as indicated above. Compressed air is introduced between the pouch and the can.

The compositions are vapourized onto dry hair. Spraying is performed in the form of a gentle spray of very good quality.

After drying, a head of hair showing very good hold is obtained.

The aerosol device does not become clogged in the course of the applications.

The invention claimed is:

1. An aerosol device, comprising:
   a) in a first compartment, a styling composition comprising at least one compound (A) chosen from hydroxypropylcelluloses and crotonic acid copolymers; and
      an alcoholic or aqueous-alcoholic medium comprising from about 20% to about 99% by weight, relative to the weight of the styling composition, of at least one $C_1$-$C_4$ monohydric alcohol, and water in an amount ranging from about 1% to about 40% by weight, relative to the total weight of the styling composition; and
   b) in a second compartment, a compressed gas chosen from air, nitrogen, carbon dioxide, and mixtures thereof.

2. The aerosol device of claim 1, wherein the compressed gas is air.

3. The aerosol device of claim 1, wherein the compressed gas has a pressure ranging from about 1 to about 12 bar.

4. The aerosol device of claim 3, wherein the compressed gas has a pressure ranging from about 9 to about 11 bar.

5. The aerosol device of claim 1, wherein the crotonic acid copolymers are chosen from vinyl acetate/vinyl tert-butylbenzoate/crotonic acid terpolymers and crotonic acid/vinyl acetate/vinyl neododecanoate terpolymers derived from maleic, fumaric or itaconic acids or anhydrides with vinyl esters, vinyl ethers, vinyl halides, phenylvinyl derivatives and acrylic acid and esters thereof, vinyl acetate/crotonic acid copolymers, and vinyl acetate/crotonic acid copolymers grafted with polyethylene glycol.

6. The aerosol device of claim 1, wherein the at least one compound (A) is present in the styling composition in an amount ranging from about 0.5% to about 20% by weight, relative to the total weight of the styling composition.

7. The aerosol device of claim 1, wherein the at least one $C_1$-$C_4$ monohydric alcohol is chosen from ethanol, isopropanol, n-propanol, tert-butanol, and mixtures thereof.

8. The aerosol device of claim 1, wherein the at least one $C_1$-$C_4$ monohydric alcohol is present in the styling composition in an amount ranging from about 20% to about 98% by weight, relative to the total weight of the styling composition.

9. The aerosol device of claim 1, wherein the styling composition is a hair lacquer.

10. A method for styling the hair comprising applying a styling composition contained in an aerosol device to wet or dry hair,
    wherein the styling composition is vaporized upon exiting the aerosol device; and
    wherein the aerosol device comprises:
    a) in a first compartment, the styling composition comprising at least one compound (A) chosen from hydroxypropylcelluloses and crotonic acid copolymers; and
       and an alcoholic or aqueous-alcoholic medium comprising from about 20% to about 99% by weight, relative to the weight of the styling composition, of at least one $C_1$-$C_4$ monohydric alcohol; and
    b) in a second compartment, a compressed gas chosen from air, nitrogen, carbon dioxide, and mixtures thereof.

* * * * *